US009110146B2

United States Patent
Czechowski et al.

(10) Patent No.: US 9,110,146 B2
(45) Date of Patent: Aug. 18, 2015

(54) METHOD TO DETERMINE ELECTRON RELAXATION TIMES, T1, IN EPR TOMOGRAPHY

(75) Inventors: Tomasz Czechowski, Poznan (PL); Mikolaj Baranowski, Poznan (PL); Kazimierz Jurga, Poznan (PL); Jan Jurga, Poznan (PL); Wojciech Chlewicki, Poznan (PL); Piotr Szczepanik, Poznan (PL); Piotr Kedzia, Poznan (PL)

(73) Assignee: POLITECHNIKA POZNANSKA, Poznan (PL)

( * ) Notice: Subject to any disclaimer, the term of this patent is extended or adjusted under 35 U.S.C. 154(b) by 725 days.

(21) Appl. No.: 13/427,261

(22) Filed: Mar. 22, 2012

(65) Prior Publication Data

US 2012/0262176 A1    Oct. 18, 2012

(30) Foreign Application Priority Data

Mar. 24, 2011 (PL) .......................... 394332

(51) Int. Cl.
*G01V 3/00* (2006.01)
*G01R 33/60* (2006.01)
*G01N 24/10* (2006.01)

(52) U.S. Cl.
CPC ................ *G01R 33/60* (2013.01); *G01N 24/10* (2013.01)

(58) Field of Classification Search
CPC ..................................................... G01R 33/60
USPC ................... 324/316, 317, 318, 322
See application file for complete search history.

(56) References Cited

U.S. PATENT DOCUMENTS

| 8,242,778 B2* | 8/2012 | Subramanian et al. ....... 324/307 |
| 8,664,955 B1* | 3/2014 | Halpern ........................ 324/316 |
| 8,816,685 B2* | 8/2014 | Vaes et al. ..................... 324/316 |

FOREIGN PATENT DOCUMENTS

| EP | 2 214 004 A1 | 8/2010 |
| EP | 2 378 281 A1 | 10/2011 |

OTHER PUBLICATIONS

Stone et al., "Oxygen in Human Tumors: Correlations between Methods of Measurement and Response to Therapy," *Radiation Research*, 1993, pp. 422-434, vol. 136, No. 3, Academic Press Inc.

Jiang et al., "Measurement of $Po_2$ in Liver Using EPR Oximetry," *J. Appl. Physiol.*, (1996) pp. 552-558, vol. 80, American Physiological Society.

(Continued)

*Primary Examiner* — Louis Arana
(74) *Attorney, Agent, or Firm* — Oliff PLC

(57) ABSTRACT

A method for determination of the images of electron relaxation times, $T_1$, in EPR tomography consists in the resultant relaxation time, $T_1$, established from the ratio of amplitudes of signals recorded for various scanning directions is found, whereupon a variability function of the resultant relaxation time, $T_1$, is found for at least two different scan frequencies, whereupon projections for the respective relaxation times are established for every point of the recorded spectra by matching functions specific for the respective relaxation times to the resultant function of variability of relaxation time, and then images are reconstructed in 1D or in 2D or in 3D depend of the experimental conditions.

9 Claims, 4 Drawing Sheets

(56) References Cited

OTHER PUBLICATIONS

Figure 1:
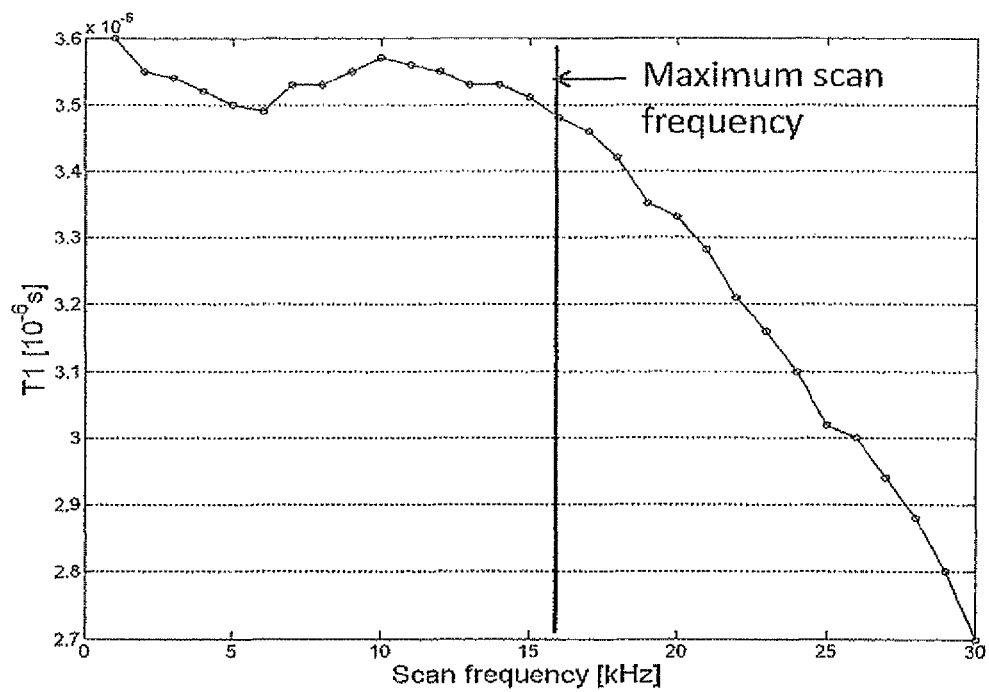

Quine et al., "A Pulsed and Continuous Wave 250 MHz Electron Paramagnetic Resonance Spectrometer," *Concepts in Magn. Reson. (Magn. Res. Engine.)*, 2002, pp. 59-91, vol. 15, Wiley Periodicals, Inc.

Maresch et al., "High Resolution ESR Imaging," *Physica*, 1986, pp. 261-263, vol. 138B Elsevier Science Publishers B.V.

Alecci et al., "Electron Paramagnetic Resonance Spectrometer for Three-Dimensional in Vivo Imaging at Very Low Frequency," *Rev. Sci. Instrum.*, 1992, pp. 4263-4270, vol. 63, No. 10, American Institute of Physics.

Halpern et al., "Imaging Radio Frequency Electron-Spin-Resonance Spectrometer with High Resolution and Sensitivity for in Vivo Measurements," *Rev. Sci. Instrum.*, 1989, pp. 1040-1050, vol. 60, No. 6, American Institute of Physics.

Sato-Akaba et al., "Half-Life Mapping of Nitroxyl Radicals with Three-Dimensional Electron Paramagnetic Resonance Imaging at an Interval of 3.6 Seconds," *Anal. Chem.*, 2009, pp. 7501-7506, vol. 81, No. 17, American Chemical Society.

Eaton et al., "EPR Imaging," *Spectroscopy*, 1986, pp. 32-35, vol. 1, No. 1.

Kuppusamy et al., "Three-Dimensional Gated EPR Imaging of the Beating Heart: Time-Resolved Measurements of Free Radical Distribution During the Cardiac Contractile Cycle," *Magn. Res. Med.*, 1996, pp. 323-328, vol. 35, Williams & Wilkins.

Lauterbur et al., "Theory and Simulation of NMR Spectroscopic Imaging and Field Plotting by Projection Reconstruction Involving an Intrinsic Frequency Dimension," Journal of Magnetic Resonance, 1984, pp. 536-541, vol. 59, Academic Press, Inc.

Maltempo, "Differentiation of Spectral and Spatial Components in EPR Imaging Using 2-D Image Reconstruction Algorithms," *Journal of Magnetic Resonance*, 1986, pp. 156-161, vol. 69, Academic Press, Inc.

Joshi et al., "Rapid-Scan EPR with Triangular Scans and Fourier Deconvolution to Recover the Slow-Scan Spectrum," *Journal of Magnetic Resonance*, 2005, pp. 44-51, vol. 175, Elsevier Inc.

Stoner et al., "Direct-Detected Rapid-Scan EPR at 250 MHz," *Journal of Magnetic Resonance*, 2004, pp. 127-135, vol. 170, Elsevier Inc.

Tseitlin et al., "Comparison of Maximum Entropy and Filtered Back-Projection Methods to Reconstruct Rapid-Scan EPR Images," *Journal of Magnetic Resonance*, 2007, pp. 157-168, vol. 184, Elsevier Inc.

Tseitlin et al., "Regularized Optimization (RO) Reconstruction for Oximetric EPR Imaging," *Journal of Magnetic Resonance*, 2008, pp. 212-221, vol. 194, Elsevier Inc.

Tseitlin et al., "Background Removal Procedure for Rapid Scan EPR," 2009, pp. 48-53, vol. 196, Elsevier Inc.

Quine et al., "A Linear Magnetic Field Scan Driver," *Concepts in Magnetic Resonance Part B (Magnetic Resonance Engineering)*, 2009, pp. 44-58, vol. 35B, Wiley Periodicals, Inc.

Subramanian et al., "A New Strategy for Fast Radiofrequency CW EPR Imaging: Direct Detection with Rapid Scan and Rotating Gradients," *Journal of Magnetic Resonance*, 2007, pp. 212-219, vol. 186, Elsevier Inc.

Ewert et al., "Spectrally Resolved EPR Tomography with Stationary Gradient," *Chemical Physics Letters*, 1986, pp. 516-520, vol. 129, No. 5, Elsevier Science Publishers B.V.

\* cited by examiner

METHOD TO DETERMINE ELECTRON RELAXATION TIMES, T1, IN EPR TOMOGRAPHY

The present invention relates to a method to determine electron relaxation times, $T_1$, in EPR tomography.

EPR (Electron Paramagnetic Resonance) imaging is capable of providing data about the pharmacokinetics of free radicals and oxygen concentration in body tissues. Detection of tissue oxygen is very important information for cancer treatment in oncology. Since free radicals are only found at low concentrations in tissues and have a very short life-time, it is assumed that at this stage of study it is necessary to introduce from the outside a free radical type with an appropriately long life-time and at a suitable concentration. Such radical compounds include Lithium phthalocyanine LiPc, which was reported in H. B, Stone, J. M. Brown, T. L. Phillips and R. M. Sutherland, Radiat. Res. 136 (1993) 422-434, J. I. Jiang, T. Nakashima, K. J. Liu, et al., J. Appl. Physiol. 80 (1996) 552-558, and of which the EPR line width largely depends on oxygen concentration in its surroundings. Standard EPR spectrometers operating at microwave frequencies are not useful for EPR imaging due to the depth of penetration of electromagnetic radiation into living matter. Consequently, lower frequencies from the radio frequency (RF) range are used in practice, which results in decreased signal-to-noise (S/N) ratios.

The imaging of small biological objects is currently based on impulse methods, which were described in R. W. Quine, G. W. Rinard, S. S. Eaton, et all, Conc. Magn. Reson. (Magn. Res. Engineer) 15 (2002) 59-91; G. G. Maresh, M. Mehring, S. Emid, Physica 138B (1986) 261-263 as well as continuous wave (CW) methods) reported by M. Alecci, S. Dellapenna, A. Sotgui, Rev. Sci. Instrum. 63 (1992) 4263-4270; H. J. Halpern, D. P. Spencer, J. van Polen, Rev. Sci. Instrum. 60 (1989) 1040-1050.

The state of art is also documented in the European Patent Applications No. 10000861.4-2209/2214004 (PL387147) and 11001983.3-2209/2378281 (PL390887) concerning methods: for localization of cancerous and atheromatous lesions by EPRI and to measure electron relaxation times $T_1$ in EPR tomography.

Standard continuous wave imaging methods are based on the use of a magnetic field gradient which is constant during scan time. After each measurement, gradient orientation rotates by a fixed angle depending on the number of projections and it is sufficient for the rotation angle to change within the 0°180° range for 2D imaging. The minimum measurement time for a single projection is 1÷2 s, however, a low signal-to-noise (S/N) ratio in the presence of the gradient requires signal accumulation which, for in vivo imaging, extends measurement time to as long as 30 minutes. Owing to recent developments in the EPR imaging techniques, the measurement time for a single projection has been reduced to ~40 ms, which has enabled reduction of the measurement time in 3D imaging to merely 3.6 s according to H. Sato-Akaba, Y. Kuwahara, H. Fujii, H. Hirata, Anal. Chem. 81 (2009), 7501-7506. The time referred to above was achieved using high resonance frequencies and the recorded signal was characterized by a high signal-to-noise (S/N) ratio; consequently, signal accumulation was not required. For the imaging of larger biological living objects it would be necessary to reduce resonance frequency to at least twice-as-low values, which would result in much lower S/N values. The changes referred to above would result in the long-term signal accumulation requirement and the total duration of measurement might increase to a minimum of 40 s, in effect. The images obtained by the method only represent the spatial distribution of the free radical, without providing any information on its surroundings. Since the EPR method is considerably more sensitive in terms of detecting changes in the local environment of radicals than MRI (Magnetic Resonance Imaging), EPR imaging is potentially more useful, compared with the MRI imaging technique. To obtain data about the surroundings of the free radical, it is necessary to acquire information not only about the spatial but also about the spectral distribution of the free radical for each projection. To this aim, an additional spectral-spatial imaging technique is used for each projection separately, as described in S. S. Eaton, G. R. Eaton, Spectroscopy 1 (1986) 32-35; U. Ewert, T. Healing, Chem. Phys. Lett. 129 (1986) 516-520; P. Kuppusamy, M. Chzhan, P. H. Weng, Magn. Res. Med. 35 (1996b) 323-328; P. C. Lauterbur, D. N. Levin, R. B. Man, J. Magn. Res. 59 (1984) 536-541; M. M. Maltempo, J. Magn. Res. 69 (1986) 156-163. In practice, this means that measurement time is extended to be several times as long, having to perform at least a few additional measurements for each gradient orientation.

A method making it possible to considerably speed up measurements is the Rapid Scan (RS) of the magnetic field, which was reported in J. P. Joshi, J. R. Ballard, J. A. Rinard, et al., J. Magn. Res. 175 (2005) 44-51; J. W. Stoner, D. Szymanski, S. S. Eaton, J. Magn. Res. 170 (2004) 127-135; M. Tsetlin, A. Dhami, S. S. Eaton, G. R. Eaton, J. Magn. Res. 184 (2007) 157-168; M. Tsetlin, T. Czechowski, S. S. Eaton, G. R. Eaton, J. Magn. Res. 194 (2008) 212-221; M. Tsetlin, T. Czechowski, R. W. Quine, S. S. Eaton, G. R. Eaton , J. Magn. Res. 196 (2009) 48-53; R. W. Quine, T. Czechowski, G. R. Eaton, Magn. Res. Eng. 35B (2009) 44-58. Instead of a second modulation of the EPR signal, the method consists in the rapid scanning of the magnetic field (at frequencies in the range 1-20 kHz), which can be performed in the sinusoidal or triangular pattern. The absence of the second modulation eliminates the need for additional phase detection, consequently, an absorption spectrum is provided rather than its first derivative. This results in reduced measurement times of a single projection, which can be as short as 50 µs. In practice, spectrum accumulation is required due to the low signal-to-noise ratio. Despite that, the traditional continuous wave method is being successfully replaced by the RS technique due to the advantage of multiple reductions of measurement times and a simplified spectrometer design.

Recent times have also seen the application of the rotational gradient technique in RS-based imaging, as described by S. Subramanian, J. Kościelniak, N. Devasahayam, J. Magn. Res. 186 (2007) 212-219, which substantially reduces measurement time. The method makes use of gradient rotation during the magnetic field scanning; in addition, the gradient rotation frequency should be at least four times as high as the scan frequency. In practice, this causes a limitation of the scan frequencies to 1 kHz.

The usefulness of impulse methods, which are widely used in NMR (Nuclear Magnetic Resonance) imaging, is limited by the very short spin-spin relaxation time, $T_2$, and spin-lattice relaxation time, $T_1$, for a majority of radicals. One of the most frequently used techniques in EPR impulse diagnostics, i.e., detection of the transverse component of magnetization, is used for measuring the relaxation times $T_2$ and $T_1$. However, as the resonance lines are significantly broadened due to the short relaxation times, such methods are not suitable for EPR imaging. Furthermore, there is the added problem of short relaxation time, $T_2$, resulting from the presence of a field gradient which, at significant gradients, will cause free induction decay (FID) during the spectrometer's dead time. The effect makes it difficult or even impossible to perform a measurement.

According to a recently proposed method [EP10000861], the projection of relaxation time, $T_1$, is determined by analysis of the ratio of amplitudes of EPR signals recorded for various scanning directions. Using scan frequencies of approx. 10 kHz, it was possible to reduce the duration of a single measurement to 100 µs. It is an advantage of the method that information on the distribution of concentration is obtained, at a time, both for the free radical and for oxygen, without having to perform any additional measurements, which are required in the spatial-spectral methods. A disadvantage of this method, as well as of the continuous wave EPR imaging methods referred to earlier, is that resultant values of relaxation times are obtained in respective projections. As an additional disadvantage, widening of the EPR line occurs, which for radicals present in the regions with different oxygen concentrations may be highly various. The effects referred to above have a considerable impact on the resolution of the reconstructed images, causing blurred images and problems with describing minor changes in the reconstructed images.

The limitations outlined above do not occur in the new method for determination of different spin-lattice relaxation times, $T_1$, based on the use of EPR spectra in the RS technique and proposed in the present solution.

A method to determine the distribution of the respective spin-lattice relaxation times, $T_1$, in EPR imaging is the objective of the present invention.

The essence of the invention is a method for determination of the images of electron relaxation times, $T_1$, in EPR tomography consisting in measuring the distribution of "spin-lattice" relaxation times of electron spins while applying to a sample a multicomponent magnetic field comprising a constant external magnetic field, a gradient field, and a scanning field, wherein the resultant relaxation time, $T_1$, established from the ratio of amplitudes of signals recorded for different scanning directions is found, whereupon a variability function of the resultant relaxation time, $T_1$, is found for at least two different scan frequencies, whereupon projections for the respective relaxation times are established for every point of the recorded spectra by matching functions specific for the respective relaxation times to the resultant function of variability of relaxation time, and then, after performing a deconvolution of the projection of the radicals for the respective relaxation times, which preferably have a shape of the Lorentz or/and Gaussian type depending on the given relaxation time and then, after obtaining a projection of the radicals' concentration, respectively, for each relaxation time, $T_1$, images are reconstructed in 1D or in 2D or in 3D.

Preferably, the variability function for the respective relaxation times, $T_1$, is established from a simulation of the Bloch equations.

Also preferably, the variability function for the respective relaxation times, $T_1$, is established by way of experimental measurements.

The application of the method of the invention has enabled the following performance and technical results to be obtained: elimination of the previously used EPR imaging techniques, based on the time-consuming spatial-spectral imaging, rotating gradient, or RS method. The method enables a separate determination of distributions for the respective relaxation times, $T_1$, whereby imaging is possible even of very small changes in oxygen concentration, which parameter characterizes the metabolism of the biological object being examined, based on the fact that the relaxation times $T_1$ and $T_2$ depend on the oxygen concentration in the surroundings of the free radical.

Figure 2:
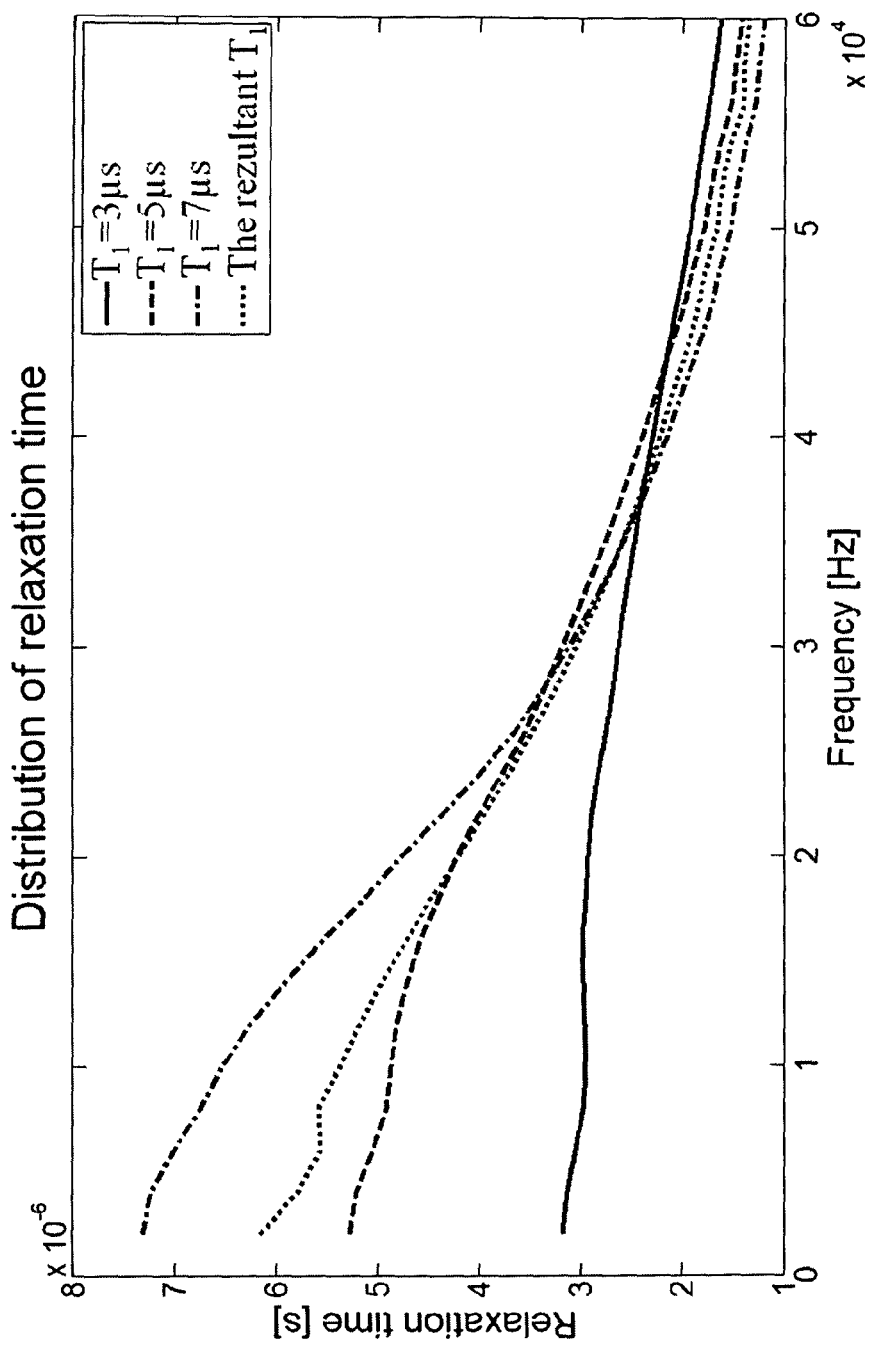
Figure 3:
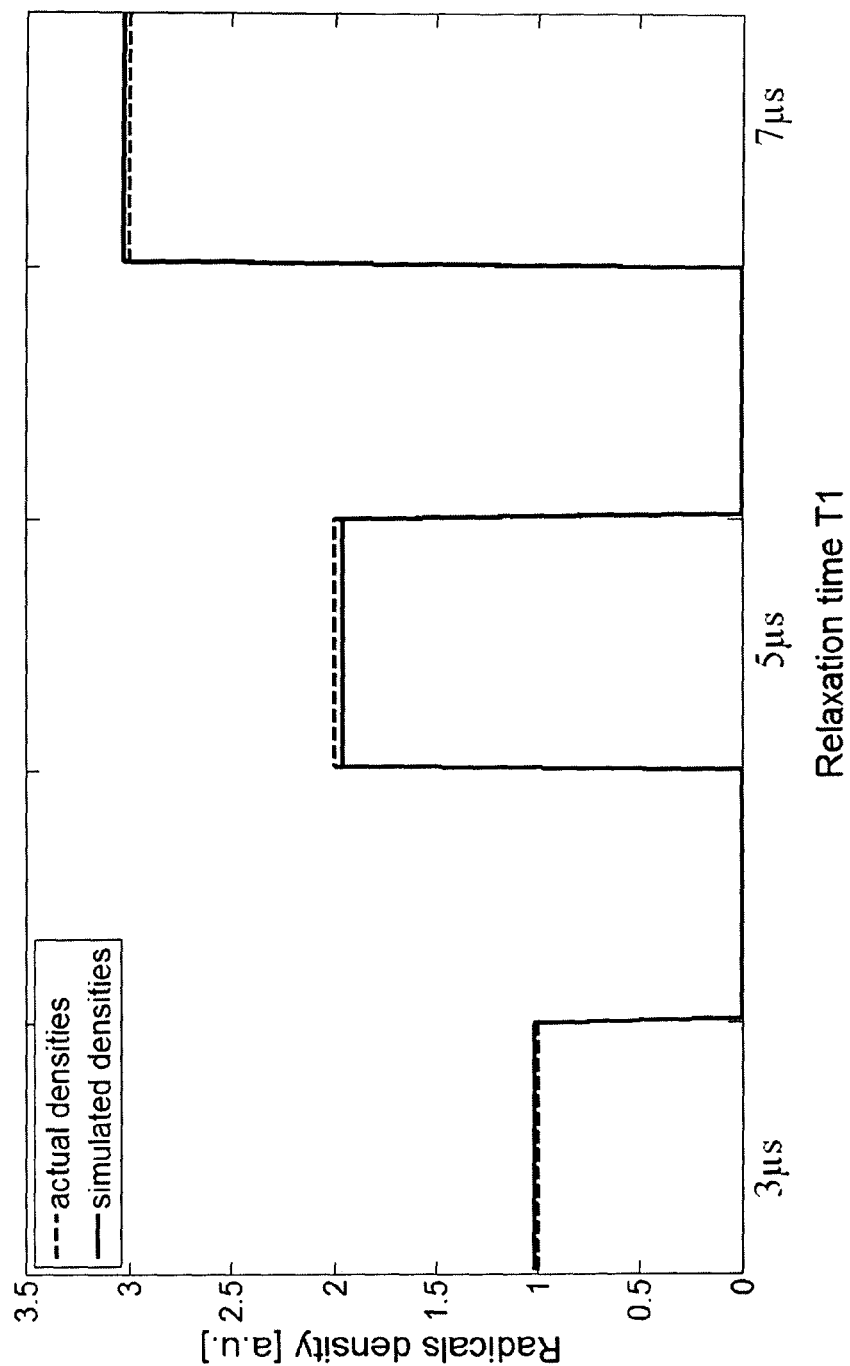
Figure 4:
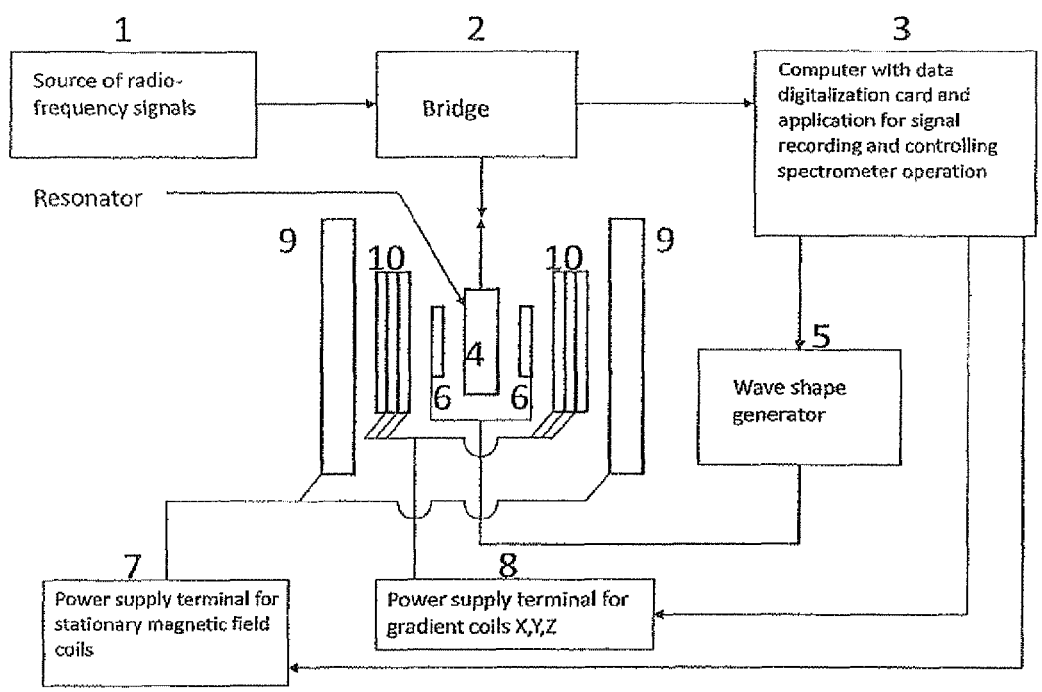

An embodiment of the present invention is illustrated by means of drawing, where:

FIG. 1 shows a theoretical graph of changes of the relaxation time, $T_1$, being determined from the ratio of amplitudes of the spectra obtained from a simulation of the Bloch equations for a radical of which the relaxation time $T_1$=3.5 µs, FIG. 2 shows theoretical graphs of changes of the relaxation times $T_1$ of which the values are 3 µs, 5 µs, 7 µs, and the resultant value, FIG. 3 shows in a graph of their resultant changes for the radical densities, FIG. 4 shows a block diagram of EPR tomography for the method's implementation.

EPR tomography for implementation of the method according to the present invention comprises a system in which a source of radio-frequency signals 1 is connected to an input of a bridge 2 whose output is connected to a computer 3 while its input/output is connected to an input/output of a resonator 4, whereas one of the outputs of the computer 3 is connected to a wave shape generator 5 which is connected to swept coils 6 and the other output of the computer 3 is connected to power supply terminals 7 and 8 of permanent magnetic field coils 9 and gradient coils 10 (FIG. 4).

After placing a sample in the resonator 4 located between the pole pieces of an electromagnet (9), the wave shape generator 5 is activated to produce a variable magnetic field with a preset shape and frequency by means of coils 6. Afterwards, a radio-frequency signal emitted by the signal source 1, via the signal detection bridge 2, is transmitted to the resonator 4. After being sent, the signal returns to the signal detection bridge 2 which transmits the separated analogue absorption and dispersion signal to the computer 3 equipped with a data digitalization card. At this stage, usual preparatory operations are performed to identify resonance conditions using a standard SWR (Standing Wave Ratio) meter. Then, using gradient coils 10, the magnetic field gradient is connected, whose orientation determines the time of EPR signal recording from the initiation of swept. In addition to signal detection, the computer 3 also controls the course of the experiment, in particular: wave shape generator 5, power supply terminals for permanent magnetic field coils 7 and 3D gradient field coils 8.

Based on the measurement of the ratio of amplitudes for spectra recorded with down and up scan, in the presence of a gradient, a projection of the resultant distribution of the relaxation time, $T_1$, is found according to a conventional method. A resultant value of relaxation time is found for every projection point, though without the possibility to determine the actual distribution of relaxation times and their weights. The above parameters are found using the proposed method for determination of electron relaxation times, $T_1$, in EPR tomography, whereby the respective relaxation times, $T_1$, are determined by measuring the ratio of amplitudes for spectra recorded with down and up scan, using rapid transitions for several different scan frequencies of the magnetic field. After determining the electron paramagnetic resonance signal in the presence of a magnetic field gradient for a specified scan frequency in a conventional manner, the ratio of amplitudes is measured for spectra recorded with down and up scan and then the resultant relaxation time, $T_1$, is found based on the measured ratio of amplitudes. In the next stage, the procedure is repeated for a different scan frequency. It appears that increasing the magnetic field scan frequency reduces the time interval between the signals recorded for down and up scan. The departure of magnetization from the equilibrium value for the test sample at the time of recording the signal is strictly connected with the relaxation time, $T_1$. The longer the relaxation time, the more difficult it is for magnetization to keep pace with the effective magnetic field, therefore, in the case of rapid transitions, the scan time should be a minimum of $16T_1$ for the correct determination of the relaxation time. If the scan time is shorter than that stated above, the measured value of relaxation time $T_1$ is shorter than actual. The above disproportion grows larger as the scan frequencies grow higher—FIG. 1. It appears that the obtained function of the measured relaxation time vs. scan frequency has a different form for different relaxation times—FIG. 2. The functions referred to above may be determined either by means of simulations based on Bloch equations or experimentally, for known relaxation time values, when functions for the respective relaxation times, $T_1$, are known.

The function which defines changes of the resultant relaxation time may be determined based on determination of the resultant relaxation time, $T_1$, from the spectrum recorded in the presence of the field gradient and repeating the procedure for several different scan frequencies. Given the resultant function and functions for the respective relaxation times, the radicals' concentrations for the respective relaxation times may be found according to a known method—FIG. 3. The above procedure is performed for every point of a projection, as measured in the presence of the gradient of the magnetic field in which the EPR signal was recorded. The gradient's orientation is changed in the next step and the entire procedure is repeated. The application of the above method provides, for every gradient's orientation, not only the resultant projection but also projections of the distribution of the radicals' concentrations for the given relaxation times.

Determination of the radicals' concentrations for the respective relaxation times provides a projection not only in its classic form by signal recording in the presence of a gradient but also separate projections related to the radicals for the specific relaxation times. This enables concentration images to be obtained for radicals due to the use of projection deconvolution with the use of an EPR line, defined for a radical having a given relaxation time. The above procedure provides images with an improved resolution, compared with those obtained in the conventional manner. Furthermore, the method referred to above enables cancerous changes to be located with better accuracy in the initial phases of the disease, when the region of the cancerous changes is still rather confined. This is related to the possibility of isolating the impact of the signal recorded from healthy tissues.

For example, for reconstructing a 2D image of oxygen concentration we can prepare 18 projections, or spectra recorded for a constant gradient value but for an orientation which is different from that of the gradient. Each projection must be determined for several different scan frequencies. Having to record several projections for a same gradient orientation extends the time of measurement, however, as the scan frequencies increase significantly for the subsequent projections, it can be assessed that the measurement time should be 4-5 times as long. Ultimately, the final time of measurement for a single magnetic field gradient orientation should be roughly as short as 10 ms whereas the total measurement time for all projections for specialist gradient coils should be only 0.2 s. For the obtaining of a complete 3D image, the measurement takes approximately 2 s.

The invention claimed is:

1. A method for determination of the images of electron relaxation times, $T_1$, in EPR tomography consisting in measuring the distribution of spin-lattice relaxation times of electron spins while applying to a being examined object, a multicomponent magnetic field comprising a constant external magnetic field, a gradient field, and a scanning field, and the examined object is located on EPR tomograph, which consists of a source of radio-frequency signals, a bridge, a computer, a resonator, a wave shape generator, swept coils, power supply terminals of permanent magnetic field coils and gradient coils, wherein the resultant relaxation times, $T_1$, determined from the ratio of amplitudes of signals, recorded during scanning the sample a periodically variable magnetic field an up and down directions, are established, whereupon a variability function of the resultant relaxation time, $T_1$, which reflects the dependency of the relaxation time on the scan frequency, is found for at least two different magnetic field scan frequencies, whereupon projections for the respective relaxation times are established for every point of the recorded spectra by matching functions specific for the respective relaxation times to the resultant function of variability of relaxation time, and then, for each relaxation time, $T_1$, an image is reconstructed in 1D or in 2D or in 3D.

2. A method according to claim 1, further performing a deconvolution of the projection of radicals for the respective relaxation times, and then, after obtaining a projection of concentration of the radicals, respectively, for each relaxation time, $T_1$, images of the density distribution are reconstructed in 1D or in 2D or in 3D.

3. A method according to claim 2, wherein performing a deconvolution of the projection of the radicals for the respective relaxation times, which have a shape of the Lorentz or/and Gaussian type depending on the given relaxation time.

4. A method according to claim 3, wherein the variability function for the respective relaxation times, $T_1$, is determined from a simulation of the Bloch equations.

5. A method according to claim 3, wherein the variability function for the respective relaxation times, $T_1$, is determined for sets of amplitudes of variable magnetic field and magnetic field scan frequency.

6. A method according to claim 2, wherein the variability function for the respective relaxation times, $T_1$, is determined from a simulation of the Bloch equations.

7. A method according to claim 2, wherein the variability function for the respective relaxation times, $T_1$, is determined for sets of amplitudes of variable magnetic field and magnetic field scan frequency.

8. A method according to claim 1, wherein the variability function for the respective relaxation times, $T_1$, is determined from a simulation of the Bloch equations.

9. A method according to claim 1, wherein the variability function for the respective relaxation times, $T_1$, is determined for sets of amplitudes of variable magnetic field and magnetic field scan frequency.

* * * * *